United States Patent [19]

Weinelt et al.

[11] Patent Number: 5,434,237
[45] Date of Patent: Jul. 18, 1995

[54] ESTER COMPOUNDS, PROCESS FOR THEIR PREPARATION AND THEIR USE

[75] Inventors: Frank Weinelt, Burgkirchen; Lothar Jaeckel, Flörsheim; Ohannes Balekdijan, Bad Homburg, all of Germany

[73] Assignee: Hoechst AG, Frankfurt, Germany

[21] Appl. No.: 191,787

[22] Filed: Feb. 3, 1994

[30] Foreign Application Priority Data

Feb. 13, 1993 [DE] Germany .................. 43 04 354.2

[51] Int. Cl.⁶ ............................................. C08G 63/02
[52] U.S. Cl. .................................. 528/272; 528/300; 528/301
[58] Field of Search .................. 528/272, 300, 301

[56] References Cited

U.S. PATENT DOCUMENTS

| | | | |
|---|---|---|---|
| 4,179,544 | 12/1979 | Newkirk et al. | 428/395 |
| 4,225,646 | 9/1980 | Cashion, Jr. | 428/290 |
| 4,227,390 | 10/1980 | Schoenenberger | 721/4 |
| 4,233,196 | 11/1980 | Sublett | 260/29.2 |
| 4,339,236 | 7/1982 | Decker et al. | 8/137 |

FOREIGN PATENT DOCUMENTS

| | | |
|---|---|---|
| 0166958 | 1/1988 | European Pat. Off. . |
| 0162530 | 4/1989 | European Pat. Off. . |
| 0538714 | 4/1993 | European Pat. Off. . |
| 861963 | 3/1961 | United Kingdom . |
| 1055641 | 1/1967 | United Kingdom . |

*Primary Examiner*—Samuel A. Acquah
*Attorney, Agent, or Firm*—Connolly & Hutz

[57] ABSTRACT

Specific ester products obtainable by esterifying a selected polyethylene glycol with a dicarboxylic acid in a molar ratio of 1:0.25 to 1 are described. The novel ester compounds are efficient and easily biodegradable spin finishes.

15 Claims, No Drawings

ESTER COMPOUNDS, PROCESS FOR THEIR PREPARATION AND THEIR USE

DESCRIPTION

The invention relates to ester compounds, a process for their preparation and their use as spin finishes. U.S. Pat. Nos. 4,179,544 and 4,227,390 disclose polyoxyalkylene glycols which during a heat treatment of spin finished synthetic fibers, such as texturing, evaporate without leaving a residue, so that their use in spin finishes results in relatively long cleaning intervals of the texturing machines used.

EP-B-162,530 discloses end-capped polyoxy-alkylene glycols which have good spin finish characteristics and are also distinguished by low residue on the fiber after heating processes.

However, all these compounds have the disadvantage that they are only moderately biodegradable and thus lead to pollution of the wastewater. Recently the demands for easily biodegradable spin finishes or textile auxiliaries have been intensified. These demands aim at eliminating the spin finishes reaching the wastewaters of textile factories by biodegradation. The term "biodegradable" is to be understood as meaning that the spin finishes are degraded biologically, for example, by the enzymes or bacteria contained in the sewage sludge of a water treatment plant. Desirably, this degradation should result in chemically simple compounds such as carbon dioxide, water, sulfate or phosphate. The biodegradability can be determined by various recognized test procedures. A suitable procedure is the river water test (OECD 301E test) and the Zahn-Wellens test (OECD 302B test).

EP-A-538,714 proposes ethoxylated diols for use as easily biodegradable spin finishes. These compounds, however, cannot fill the gap completely. For, if their molecular weight is above 1200, they are no longer very easily biodegradable. On the other hand, the ethoxylated diols described which have molecular weights below 1200 are problematical as texturing finish, since they exhibit insufficient stability to pressure, as a result of which they do not give the filament sufficient protection during the high mechanical stress of the texturing process. This results in production problems and losses in quality during texturing in the form of fluff-balls and yarn and filament breaks. A further disadvantage of diols having a low degree of ethoxylation and of ethylene oxide/propylene oxide compounds very generally is their tendency to swell polyurethane materials which are present in texturing machines in the form of rollers, aprons or texturing disks, resulting in premature wear of the machines. Among those skilled in the art, the measure of the polyurethane compatibility of a texturing finish is the weight increase (swelling) of the polyurethane material ® Simritan 80 AU 991 (®=registered trademark of Freudenberg) after seven days of storage in the finish to be tested at 90° C., which weight increase should be at most 10%. It may also be mentioned that although swelling of the ethoxylated diols mentioned and of ethylene oxide/propylene oxide compounds decreases with increasing molecular weight, biodegradability decreases.

Surprisingly, it has been found that specific ester compounds constitute good spin finishes and are also easily biodegradable.

The ester compounds according to the invention have the formula I below

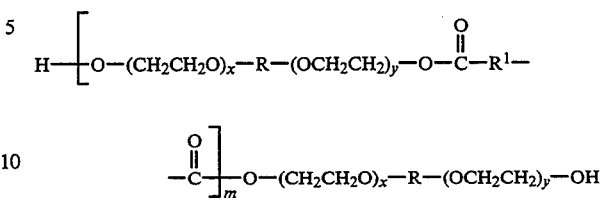

in which
R is an ethylene radical or an alkylene radical which has 2 to 4 carbon atoms in the alkylene chain and is substituted by one or more alkyl substituents, preferably one or two alkyl substituents, the alkyl substituent being methyl, ethyl, propyl or isopropyl and methyl being preferred, x plus y is 2 to 35, neither x nor y being zero, $R^1$ is —$(CH_2)_z$—, in which z is zero or an integer from 1 to 12, or is a phenylene radical or vinylene radical, and m is 1 to 30.

Preferred compounds of the formula I are those in which
R is an ethylene radical —$CH_2$—$CH_2$—, a 1-methylethylene radical (isopropylene radical), 1-methylpropylene radical, 2-methylpropylene radical or a 2,2-dimethylpropylene radical, the isopropylene radical being particularly preferred, x plus y, i.e. the sum of x and y, is 5 to 22, neither x nor y being zero, $R^1$ is —$(CH_2)_z$—, in which z is 1 to 8, or is a phenylene radical or vinylene radical, and m is 1 to 10.

The oligoesters of the formula I are obtained by esterification of a diol of the formula II below

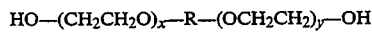
HO—$(CH_2CH_2O)_x$—R—$(OCH_2CH_2)_y$—OH in which R, x and y have the meaning given in formula I with a dicarboxylic acid of the formula III below
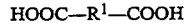
HOOC—$R^1$—COOH in which $R^1$ has the meaning given in formula I in a molar ratio of 1:0.25 to 1, preferably 1:0.45 to 1.

Suitable diols or polyethylene glycols are preferably those of the formula II having a molecular weight of 200 to 1500, preferably 300 to 1000. Particularly preferred diols are those in which R is isopropylene, i.e. those obtained from isopropylene glycol as starting material. Polyethylene glycols of this type and their preparation are described in EP 0,166,958 B1. They are preferably prepared such that the glycol compound which corresponds to the radical R in formula II, for example ethylene glycol or isopropylene glycol, is introduced first and reacted with a number of moles of ethylene oxide corresponding to the desired sum of x plus y in formula II. As a rule, the detailed procedure is such that the glycol compound and an alkaline catalyst are introduced first into a pressure vessel equipped with a stirrer, and the vessel is then flushed, preferably with nitrogen, in order to produce an inert atmosphere. Any water which may be present is removed by applying vacuum. At 110°–170° C., preferably 120°–160° C., the ethylene oxide adduct is then formed by metering in liquid or gaseous ethylene oxide at the autogenous pressure. The end of ethylene oxide addition is indicated by a drop in pressure, the pressure remaining essentially constant. To remove volatiles which may be present, the polyethylene glycol obtained is maintained at about 80° to 120° C. for 0.3 to 1 hour under a vacuum. Preferred alkylene catalysts are sodium hydroxide, sodium carbonate or sodium methoxide and the corresponding potassium compounds. The amount of catalyst is in general 0.1 to 5% by weight, preferably 0.3 to 3% by weight, relative to the amount of glycol compound used.

The dicarboxylic acids to be used can be of aromatic or aliphatic nature. The aliphatic dicarboxylic acids may be saturated or unsaturated. The aromatic dicarboxylic acid is preferably phthalic acid (benzene-ortho-dicarboxylic acid), terephthalic acid (benzene-para-dicarboxylic acid) and isophthalic acid (benzene-meta-dicarboxylic acid). The aliphatic saturated dicarboxylic acid is preferably one containing $C_1$–$C_8$-alkylene groups, such as malonic acid, succinic acid, glutaric acid, adipic acid, pimelic acid, suberic acid, azelaic acid and sebacic acid. The aliphatic unsaturated dicarboxylic acid is preferably fumaric acid or maleic acid. Of the dicarboxylic acids mentioned, the aliphatic saturated dicarboxylic acids and maleic acid are preferred. It goes without saying that instead of the dicarboxylic acids derivatives thereof can also be used, for example the corresponding anhydrides and halides, the anhydrides (dicarboxylic anhydrides) being preferred.

Esterification of the diols of the formula II with the dicarboxylic acids or dicarboxylic anhydrides of the formula III is preferably carried out in the absence of solvents (i.e. in substance) and under a blanket of inert gas, the water of reaction being distilled off from the reaction mixture. The esterification temperatures are 170° to 230° C., preferably 180° to 210° C. The esterification reaction is preferably carried out with acid or weakly acid catalysis. Acid catalysis is obtained, for example, with p-toluenesulfonic acid, methanesulfonic acid and hypophosphorous acid or mixture thereof as the catalyst. Weakly acid catalysis is obtained, for example, by using a molar 1:1 mixture of hypophosphorous acid and NaOH (solid or in the form of a, for example, 1 to 50% by weight aqueous solution) as the catalyst. A particularly preferred catalyst is a mixture of p-toluenesulfonic acid or methanesulfonic acid and hypophosphorous acid in a weight ratio of 1:0.5, when the hypophosphorous acid is used as such (i.e. as a 100% acid), or in a weight ratio of 1:1, when the hypophosphorous acid is used in the form of an approximately 50% by weight aqueous solution. This catalyst provides oligoesters of particularly good color quality and without precipitate. The amount of catalyst can be varied within wide limits. It is in general 0.03 to 0.5% by weight, relative to the weight of diol and dicarboxylic acid or dicarboxylic anhydride, preferably 0.05 to 0.2% by weight.

The end of the esterification reaction is indicated by the acid number of the esterification product, which should be smaller than 5, preferably smaller than 3 and particularly preferably 0.3 to 2.5. The esterification product obtained, which, after cooling to room temperature, is, if desired, subjected to filtration, represents the desired spin finish. In general, the product has a viscosity of greater than 500 mPas at 20° C., preferably 700 to 5000 and particularly preferably 900 to 3000 mPas at 20° C. Further characteristic data of the oligoesters according to the invention are the OH number (number of hydroxy groups), the saponification number, and the iodine number. The OH number is in general 10 to 160, preferably 70 to 115, the saponification number 40 to 300, preferably 50 to 220, and the iodine number less than 0.1 to 20, preferably less than 0.1 to 8 and particularly preferably less than 0.1 to 1.

The ester products according to the invention can be used as such, i.e. on their own, or in a mixture with other spin finishes known per se during fiber production and/or treatment. This means that the spin finish according to the invention is composed of up to 100% by weight of the ester compounds of the formula I or, in other words, the spin finish according to the invention contains or is composed of the ester compounds of the formula I. The mixing components used can be the known and customary ones, such as ethylene oxide/propylene oxide polymers, surfactants, ester oils obtained from fatty alcohols and fatty acids, phosphoric esters and salts thereof, ethoxylates of lower alkanols or alkane diols, fatty alcohol ethoxylates, fatty amine ethoxylates and/or fatty acid ethoxylates, which serve, for example, as lubricants, wetting agents, emulsifiers, yarn cohesifiers and/or antistats. In mixtures with other components, the amount of compounds of the formula I is in general 5 to 95% by weight, preferably 30 to 60% by weight, % by weight based on the (ready-to-use) spin finish. Thus, a preferred mixture according to the invention consists essentially of a) 30 to 60% by weight of an ester product of the formula I,
b) 5 to 20% by weight of a saturated or unsaturated, linear or branched $C_8$–$C_{18}$-alcohol ethoxylated with 5 to 15 ethylene oxide units, and
c) 20 to 50% by weight of a diol of the abovementioned formula II, % by weight being based on the (ready-to-use) mixture.

When the ester product according to the invention or mixtures thereof or mixtures of the ester product according to the invention with other known spin finishes are used as spin finish, they are applied to the fiber in an amount of, in general, 0.1 to 1% by weight, preferably in an amount of 0.3 to 0.5% by weight, % by weight being based on the weight of the (treated) fiber. The fiber material is preferably made of polyesters, polyamides, polyacrylonitriles, polyolefins or copolymers thereof. The spin finishes according to the invention are preferably applied to the fiber material in such a manner that the spin finish is sprayed onto the fiber or the fiber is led through a bath in which the spin finish is present as such or in the form of a preferably 10 to 30% by weight solution, emulsion or dispersion.

The oligoester product exhibits a number of advantages. It has unexpectedly good biodegradability. This is all the more surprising as the compounds have a complicated structure and a relatively high molecular weight. Furthermore, the ester product according to the invention forms only minimal residues during heating processes and causes only very little swelling in polyurethane. On using the ester products described as spin finishes, they thus exhibit the required characteristics; they also produce thread-protecting elasticity, which is a particularly desirable property. This means that the ester products according to the invention and their mixtures simultaneously have the advantages of high biogradability in combination with little swelling of polyurethane materials, little tendency to form residues, and the required thread-protecting elasticity under pressure. Accordingly, they are highly suitable for use as spin finishes, preferably as texturing finish and as component of texturing finishes. The oligoesters according to the invention are in general water-soluble or water-dispersible.

The invention will now be illustrated by way of example. Preparation of the ester compounds according to the invention:

Example 1

A reaction vessel equipped with thermometer, water separator fitted with reflux condenser, stirrer and heating unit was charged with 600 g (1 mol) of a diol of the formula II where R is isopropylene and x plus y is 12 (molecular weight of 600), 50 g (0.5 mol) of succinic anhydride, and 0.9 (0.14% by weight, relative to the sum of the weight of diol and succinic anhydride) of a mixture of p-toluenesulfonic acid and hypophosphorous acid in a weight ratio of 1:0.5 as the catalyst. The initial charge was heated to 200° C. under a nitrogen atmosphere and maintained at a temperature of 190° to 210° C. with continuous removal of water (about 6 hours) until the esterification product had an acid number of about 0.7, thus resulting, after cooling, in the oligoester product according to the invention.

Examples 2 to 16

Further products according to the invention were prepared under reaction conditions analogous to those in Example 1.

Table I below summarizes Examples 1 to 16, for which the starting materials, diol and dicarboxylic acid, the molar ratio used of diol to dicarboxylic acid, and the following properties of the oligoester product obtained are listed: Acid number (AN), hydroxyl number (OHN), saponification number (SN), iodine number (IN), and viscosity (VSC) in mPa×s at 20° C. The diols used are designated in Table I by, for example, "PEG600PR" (Example 1) or "PEG300PR" (Example 3), which means that they are a polyethylene glycol (PEG) of molecular weight 600 and 300, respectively, the starting material being isopropylene glycol (PR). The diols designated in Table I by, for example, "PEG300ET" (Example 5) or "PEG600ET" (Example 6) are polyethylene glycols (PEG) of molecular weight 300 and 600, respectively, the starting material being ethylene glycol (ET). The diols used are further characterized in terms of the sum of x and y as per the formula II.

Testing of the ester compounds according to the invention for suitability as spin finishes: Of the ester products prepared in Examples 1 to 16, those from Examples 1, 3 and 5 were tested as representatives of all the others for swelling of polyurethane, evaporation and biodegradability; the ester product from Example 1 was also tested for suitability as texturing finish.

Testing of the swelling of polyurethane material Simritan 80 AU 991 ( =registered trademark of Freudenberg):

The weight increase observed after storing samples of the polyurethane mentioned in the ester product from Examples 1, 3 and 5° at 90° C. for seven days was determined. A comparative test was carried out using the diol employed in Example 1. The results are summarized below:

| Example | Weight increase |
|---|---|
| 1 | 7% |
| 3 | 6% |
| 5 | 6% |
| comparison | 15% |

Testing of the continual rate of evaporation:

In the evaporation test, 1 g each of the ester product from Examples 1, 3 and 5 was maintained at 220° C., and the loss, expressed in % by weight, was determined after 0.33 hour (20 minutes) and 24 hours. The results are summarized below:

| Example | 20 minutes | 24 hours |
|---|---|---|
| 1 | 5% | >90% |
| 3 | 4% | >90% |
| 5 | 3% | >90% |

Testing for biodegradability:

Biodegradability was determined by the OECD 301E test and the OECD 302B test (determination of biological elimination as a function of time). Below, the maximum values of biodegradability after 28 days are shown for the ester products from Examples 1, 3 and 5:

| Example | OECD 301E Test | OECD 302B Test |
|---|---|---|
| 1 | 80% | 100% |
| 3 | 64% | 100% |

TABLE 1

| Example | Diol | Dicarboxylic acid | Diol/dicarboxylic acid molar ratio | AN | OHN | SN | IN | VSC |
|---|---|---|---|---|---|---|---|---|
| 1 | PEG600PR/x + y = 12 | succinic acid | 1:0.5 | 0.7 | 80 | 88 | <0.1 | 1085 |
| 2 | PEG450PR/x + y = 8.5 | succinic acid | 1:0.5 | 0.7 | 111 | 116 | <0.1 | 762 |
| 3 | PEG300PR/x + y = 5 | succinic acid | 1:0.5 | 2.3 | 98 | 170 | <0.1 | 708 |
| 4 | PEG1000PR/x + y = 21 | succinic acid | 1:0.5 | 1.0 | 55 | 55 | <0.1 | 1372 |
| 5 | PEG300ET/x + y = 5.8 | succinic acid | 1:0.5 | 0.3 | 151 | 163 | <0.1 | 715 |
| 6 | PEG600ET/x + y = 12.6 | succinic acid | 1:0.5 | 0.4 | 81 | 90 | <0.1 | solid |
| 7 | PEG600PR/x + y = 12 | succinic acid | 1:0.45 | 0.6 | 88 | 80 | <0.1 | 865 |
| 8 | PEG300PR/x + y = 5 | succinic acid | 1:0.67 | 1.2 | 110 | 215 | <0.1 | 1240 |
| 9 | PEG300PR/x + y = 5 | succinic acid | 1:1 | 3.7 | 15 | 296 | <0.1 | >10000 |
| 10 | PEG600PR/x + y = 12 | adipic acid | 1:0.5 | 1.2 | 83 | 77 | 0.4 | 908 |
| 11 | PEG600PR/x + y = 12 | azelaic acid | 1:0.5 | 1.2 | 83 | 77 | 0.4 | 908 |
| 12 | PEG600PR/x + y = 12 | glutaric acid | 1:0.5 | 4.0 | 85 | 86 | 1.0 | 803 |
| 13 | PEG600PR/x + y = 12 | maleic acid | 1:0.5 | 3.6 | 90 | 86 | 20 | 983 |
| 14 | PEG300PR/x + y = 5 | oxalic acid | 1:0.5 | 2.2 | 112 | 43 | 5.5 | 190 |
| 15 | PEG600PR/x + y = 12 | phthalic acid | 1:0.5 | 1.9 | 77 | 91 | 5.6 | 1602 |
| 16 | PEG300PR/x + y = 5 | terephthalic acid | 1:0.5 | 1.5 | 150 | 162 | 7.5 | 1614 |

-continued

| Example | OECD 301E Test | OECD 302B Test |
|---------|----------------|----------------|
| 5       | 71%            | 100%           |

Testing for suitability as texturing finish:

Three products according to the invention were subjected to a texturing test, the ester product from Example 1 (Product 1), a mixture of 85% by weight of the ester product from Example 1 and 15% by weight of a fatty alcohol ethoxylated with 8 mol of ethylene oxide (Product 2), and a mixture of 30% by weight of the ester product from Example 5, 20% by weight of a fatty alcohol ethoxylated with 8 mol of ethylene oxide, and 50% by weight of the ethoxylated diol used in Example 1 (Product 3). For comparison, a customary polyoxyalkylene glycol and the ethyoxylated diol used in Example 1 were tested.

In each case, the test product was applied by means of a gear pump to a polyester fiber as it was being spun. Details of the test procedure and texturing data are given below:

Texturing machine: Barmag FK 6/700
Linear density of extruded material: Polyester, POY (partially orientated yarn) 260 dtex f32 matt
Add-on: 0.35 % by weight
Speed: 620 m per minute
Spindle: Friction unit, ceramic disk
Draw ratio: 1.59
D/y (Circumferential speed of the friction disk divided by the supply speed of the yarn): 2.2
Temperature of the two heating units: 205° and 180° C.
$T_1/T_2$ (Yarn tension before entering the machine and thread tension after leaving the machine): 62 cN and 65 cN.

The tests were then evaluated by the overall number of irregularities in the form of fluffballs, yarn breaks and filament breaks during 100 km of fiber production. The number of irregularities in the products tested is listed below:

| Test product | Number of irregularities |
|--------------|--------------------------|
| Product 1    | 10                       |
| Product 2    | 8                        |
| Product 3    | 4                        |
| Polyoxyethylene glycol | 21             |
| Ethoxylated diol | 260                  |

The test results show that the ester products according to the invention exhibit an excellent combination of properties with respect to their use as spin finish.

What is claimed is:

1. An ester compound consisting of the formula I below

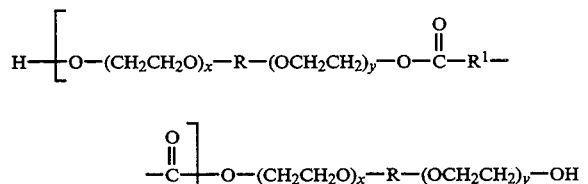

in which

R is an ethylene radical or an alkylene radical which has 2 to 4 carbon atoms in the alkylene chain and is substituted by one or more alkyl substituents, the alkyl substituent being methyl, ethyl, propyl or isopropyl, x plus y is 2 to 35, neither x nor y being zero, $R^1$ is —$(CH_2)_z$—, in which z is zero or an integer from 1 to 12, or is a phenylene radical or vinylene radical, and m is 1 to 30.

2. An ester compound as claimed in claim 1, wherein R is an ethylene radical or an alkylene radical which has 2 to 4 carbon atoms in the alkylene chain and is substituted by 1 or 2 alkyl substituents, the alkyl substituent being methyl.

3. An ester compound as claimed in claim 1, wherein R is an ethylene radical, 1-methylethylene radical, 1-methylpropylene radical, 2-methylpropylene radical or 2,2-dimethylpropylene radical, x plus y is 5 to 22, neither x nor y being zero, $R^1$ is —$(CH_2)_z$—, in which z is 1 to 8, or is a phenylene radical or vinylene radical, and m is 1 to 10.

4. An ester compound as claimed in claim 1, wherein R is a 1-methylethylene radical.

5. An ester compound as claimed in claim 1, wherein R is a 1-methylethylene radical, x plus y is 5 to 22, neither x nor y being zero, $R^1$ is —$(CH_2)_z$—, in which z is 1 to 8, or is a phenylene radical or vinylene radical, and m is 1 to 10.

6. A process for preparing an ester compound as claimed in claim 1, consisting essentially of esterifying a diol of the formula II below $$HO-(CH_2CH_2O)_x-R-(OCH_2CH_2)_y-OH$$

in which R, x and y have the meaning given in formula I of claim 1, with a dicarboxylic acid of the formula III below $$HOOC-R^1-COOH$$

in which $R^1$ has the meaning given in formula I of claim 1, in a molar ratio of 1:0.25 to 1.

7. The process as claimed in claim 6, wherein the diol and the dicarboxylic acid are used in a molar ratio of 1:0.45 to 1.

8. The process as claimed in claim 6, wherein esterification is carried out at a temperature of 170° to 230° C. and up to an acid number of the esterification product of less than 5.

9. The process as claimed in claim 6, wherein esterification is carried out at a temperature of 170° to 230° C. and up to an acid number of the esterification product of less than 3.

10. The processes as claimed in claim 9, wherein the esterification is carried out at a temperature of 170°–230° C. and up to an acid number of the esterification product between 0.3 to 2.5.

11. The ester compound as claimed in claimed 1, wherein said ester has a viscosity greater than 500 mPas at 20° C., the number of hydroxy groups in said ester is from 10 to 160, the saponification number is from 40 to 300 and the iodine number is 0.1 to 20.

12. The ester compound as claimed in claimed 1, wherein said ester has a viscosity of 700–5,000 mPas at 20° C., the number of hydroxy groups in said ester is from 70 to 115, the saponification number is from 50 to 220 and the iodine number is from 0.1 to 8.

13. The ester compound as claimed in claimed 5, wherein said ester has a viscosity of 900–3,000 mPas at 20° C., the number of hydroxy groups in said ester is from 70 to 115, the saponification number is from 50 to 220 and the iodine number is from 0.1 to 1.

14. The process as claimed in claim 9, wherein said ester has a viscosity of 900–3,000 mPas at 20° C., the number of hydroxy groups in said ester is from 70 to 115, the saponification number is from 50 to 220 and the iodine number is from 0.1 to 1.

15. A process for preparing an ester compound as claimed in claim 1, which consists of esterifying a diol of the formula II below $$HO-(CH_2CH_2O)_x-R-(OCH_2CH_2)_y-OH$$

in which R, x and y have the meaning given in formula I of claim 1, with a dicarboxylic acid of the formula II below $$HOOC-R^1-COOH$$

in which $R^1$ has the meaning given in formula I of claim 1, in a molar ratio of 1:0.25 to 1.

* * * * *